United States Patent
Sun et al.

(10) Patent No.: US 8,723,104 B2
(45) Date of Patent: May 13, 2014

(54) METHODS AND MEANS FOR MANIPULATING PARTICLES

(75) Inventors: Dong Sun, Kowloon (HK); Xiaolin Wang, Kowloon (HK)

(73) Assignee: City University of Hong Kong, Hong Kong (HK)

( * ) Notice: Subject to any disclaimer, the term of this patent is extended or adjusted under 35 U.S.C. 154(b) by 0 days.

(21) Appl. No.: 13/613,725

(22) Filed: Sep. 13, 2012

(65) Prior Publication Data

US 2014/0073000 A1 Mar. 13, 2014

(51) Int. Cl.
*G21K 5/04* (2006.01)
*G21K 1/00* (2006.01)
*G01N 21/17* (2006.01)

(52) U.S. Cl.
CPC *G21K 1/00* (2013.01); *G01N 21/17* (2013.01); *G21K 1/003* (2013.01); *G21K 1/006* (2013.01)
USPC .......... 250/251; 209/1; 209/2; 209/8

(58) Field of Classification Search
CPC ......... G21K 1/00; G21K 1/003; G21K 1/006; B07B 13/003; G01N 21/00; G01N 21/17
USPC ........ 250/251; 209/1, 2, 8, 12.1, 13, 132, 571
See application file for complete search history.

(56) References Cited

U.S. PATENT DOCUMENTS

| | | | |
|---|---|---|---|
| 7,894 A | 1/1851 | Warner | |
| 171,846 A | 1/1876 | Pease | |
| 177,940 A | 5/1876 | Holbrook | |
| 6,778,724 B2 | 8/2004 | Wang et al. | |
| 7,068,874 B2 | 6/2006 | Wang et al. | |
| 7,137,574 B2 | 11/2006 | Grier et al. | |
| 7,233,423 B2 | 6/2007 | Grier | |
| 7,428,971 B2 | 9/2008 | Hirano et al. | |
| 7,699,767 B2 | 4/2010 | Mueth et al. | |
| 2004/0089798 A1* | 5/2004 | Gruber et al. | 250/251 |
| 2004/0248167 A1* | 12/2004 | Quake et al. | 435/6 |
| 2009/0032449 A1* | 2/2009 | Mueth et al. | 210/94 |

OTHER PUBLICATIONS

Lin, Chen-Chen et al., Microfluidic cell counter/sorter utilizing multiple particle tracing technique and optically switching approach, Biomed Microdevices, vol. 10, 2008, pp. 55-63.

Murata, Masaya et al., Cell separation by the combination of microfluidics and optical trapping force on a microchip, Anal Bioanal Chem, vol. 394, 2009, pp. 277-283.

Veenman, Cor J. et al., Resolving Motion Correspondence for Densely Moving Points, IEEE Transactions on Pattern Analysis and Machine Intelligence, vol. 23, No. 1, Jan. 2001, pp. 54-72.

* cited by examiner

*Primary Examiner* — Nicole Ippolito
(74) *Attorney, Agent, or Firm* — Melvin S. Li; Heslin Rothenberg Farley & Mesiti P.C.

(57) ABSTRACT

The present invention is concerned with a system for sorting target particles from a flow of particles. The system has a microscope, a light source, a CCD camera, microfluidic chip device with microfluidic channels, a detection apparatus for detecting the target particles with predefined specific features, a response generating apparatus for generating a signal in response to the detection of the target particles, and an optical tweezing system for controlling movement of optical traps, the optical tweezing system is operably linked to the response signal.

13 Claims, 6 Drawing Sheets

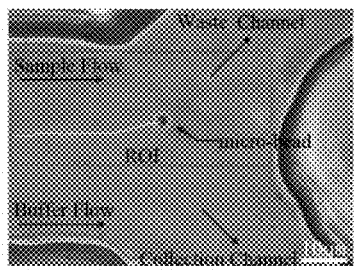  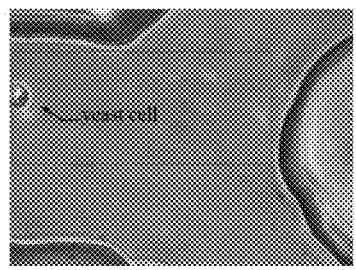
Fig. 10a                Fig. 10b                Fig. 10c
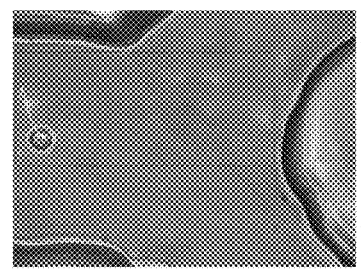  
Fig. 10d                Fig. 10e                Fig. 10f
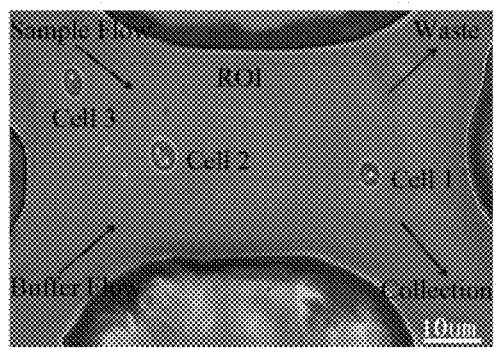
Fig. 11
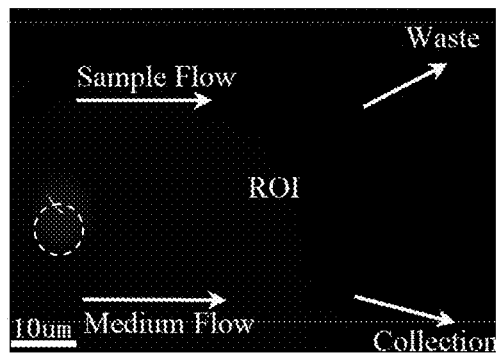 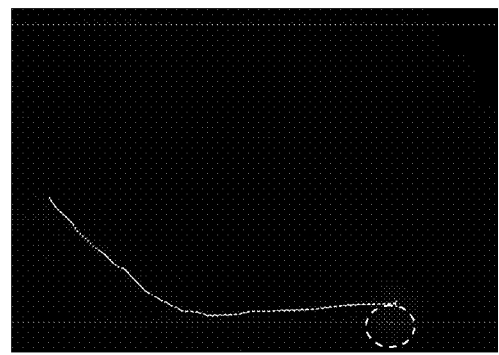
Fig. 12

METHODS AND MEANS FOR MANIPULATING PARTICLES

FIELD OF THE INVENTION

The present invention is concerned with methods and means for manipulating particles, and in particular but not limited methods and means for sorting particles such as cells, micro-beads and the like in a flow of particles.

BACKGROUND OF THE INVENTION

There are conventional systems designed to separate target particles, e.g. cells, from a flow of particles. While these systems are effective to a certain extent they often suffer from one problem or another. For example, some of the conventional systems are limited in that they cannot sort multiple particles at the same time. Other systems rely on overly simplistic assumption of motion behavior of particles or biological particles (which often have intrinsic heterogeneity of motion). There are also systems which rely on computational intensive calculation for tracking or identifying the particles and this render such systems unsuitable for real-time processing of separation of particles in continuous particle flow.

The present invention seeks to address these problems or at least to provide an alternative to the public.

SUMMARY OF THE INVENTION

According to a first aspect of the present invention, there is provided a method of manipulating flowing particles, comprising steps of a) providing fluid channels in which a laminar flow of suspended particles moving at constant speed is to be sorted, b) providing region of interest in the fluid channels via which the flow of particles pass, c) based on methodology of capturing image of the flow of particles, detecting individual first order motions of flowing particles and tracking movement of multiple particles of the flowing particles in the region of interest by using imaging processing technique, d) based on results from image processing of aforementioned step c), determining the presence of at least one target particle from the flow of particles, e) triggering the generation of an optical trapping means and changing the course of the at least one target particle transversely from a first flow stream to a second flow stream by the optical trapping means, and f) labeling the at least one target particle.

Preferably, the method may comprise moving the at least one target particle to a target location by the optical trap.

In an embodiment, the method may comprise determining whether the at least one target particle has been moved to the target location, and if the at least one target particle has been moved to the target location the optical trapping means is released from the target particle, and if the at least one target particle has not been moved to the target location data associated with current position of the target particle(s) is updated within a database.

In one embodiment, the method may comprise a step of recording center position of the at least one target particle as current image frame.

The method may further comprise the steps of:
i) calculating the distance between the at least one target particle in current image frame and a respective labeled particle in previous image frame;
ii) ascertaining whether the distance in step i) is less than a predefined distance; and
iii) assigning same label of the respective labeled particle for the at least one target particle in current frame if the distance in step j) is less than the predefined distance; or assigning new label for the at least one target particle in current frame if the distance in step g) is equal or greater than the predefined distance.

Suitably, in step c), the image processing technique may be adapted to identify particles based on intrinsic features such as morphology, sizes, etc. of the particles. The image processing technique may also be adapted to identify particles based on extrinsic features such as fluorescence labeling, tagging, etc. on the particles.

Suitably, the method may comprise a step of measuring the velocity of the at least one target particle in the laminar flow.

The image processing technique may also be adapted to distinguish multiple target particles and track multiple target particles in the region of interest.

The optical trapping means may include at least one optical trap, and wherein the number of optical traps employed corresponds to the number of detected target particles in the region of interest and the capacity of the optical trapping means.

The method may comprise a step of providing a branching junction in the fluid channels, wherein the at least one optical trap is movable or moves diagonally along the branching junction for translating the at least one target cell into a target channel of the fluid channels.

Suitably, the velocity of the optical trap and the velocity of the laminar flow in the flowing direction along the branching junction may be substantially the same.

In step e), the step of changing the course of the at least one target particle may include a series of successive steps, and wherein in each of the successive steps the optical trapping means may be adapted to move the at least one target particle by a distance equal to the radius of the target particle and perpendicular to the laminar flow.

According to a second aspect of the present invention, there is provided a system for sorting target particles from a flow of particles, comprising:
a) a microscope;
b) a light source;
c) a CCD camera;
d) microfluidic chip device with microfluidic channels;
e) a detection apparatus for detecting the target particles with predefined specific features;
f) a response generating apparatus for generating a signal in response to the detection of the target particles; and
g) an optical tweezing system for controlling movement of optical traps, the optical tweezing system is operably linked to the response signal.

Preferably, the microfluidic chip device may include a cover glass layer, a PDMS microfluidic chip layer and a fluid flow controller. The PDMS microfluidic chip layer may be provided with a plurality of reservoirs and a plurality of the microfluidic channels.

The optical tweezing system may include holographic optical tweezers.

BRIEF DESCRIPTION OF DRAWINGS

The present invention will now be explained below, with reference to the drawings, in which:—

FIGS. 10a-f, are successive images demonstrating separation of yeast cells (target particles) from micro-beads when using an embodiment of a methodology according to the present invention;

FIG. 11, including two successive images, illustrates, exemplarily, sorting multiple yeast cells (target particles) using multiple independent optical traps simultaneously according to the present invention; and FIG. 12, including two successive images, illustrates, exemplarily, sorting hESCs with green fluorescent protein (GFP, circled cell in figure, target particle) from the other cells without fluorescence labels according to the present invention.

DETAILED DESCRIPTION OF THE PREFERRED EMBODIMENT OF THE PRESENT INVENTION

The present invention is generally concerned with methods and means for use in separating target particles such as cells, micro-beads and the like from a flow of particles from a relatively small particle population. The means comprises a sorting apparatus or sorter equipped with movable or moving optical tweezers in a microfluidic chip. The design of the sorter is based on fluid dynamic and light pattern dynamic, which enable the sorting of micro-particles such as cells from a small amount of sample with high accuracy. The microfluidic chip is provided with design of a microfluidic channel system. A laminar fluid flow is generated within the system and this can enhance sorting performance in the system. With the use of image processing technique, the particles within the fluid flow can be optically identified based on intrinsic or extrinsic traits thereof. With the use of multiple tracking strategies, a number of particles can be tracked and sorted simultaneously. The ability of tracking and sorting multiple particles can improve throughput of the system without compromising the recovery rate and purity of the sorted particles. The optical tweezers are able to generate optical trap when detection of target particles have been triggered. The optical tweezers can translate or move the target particles transverse from one flow stream to another flow stream over a certain distance. Non-target particles not having been trapped will flow with the primary flow stream without altering its motion trajectory. Motion of the optical trap in the flowing fluid can be optimized to improve efficiency of trapping of the target particles. The efficiency of trapping of the target particles is increased by calibrating the relationship between the maximum moving velocity of the target particles and the laser power. The following will describe the present invention in a more detailed manner in the context of different embodiments. Experiments on sorting of biological particles performed to demonstrate the effectiveness of the present invention are also described.

Figure 1:
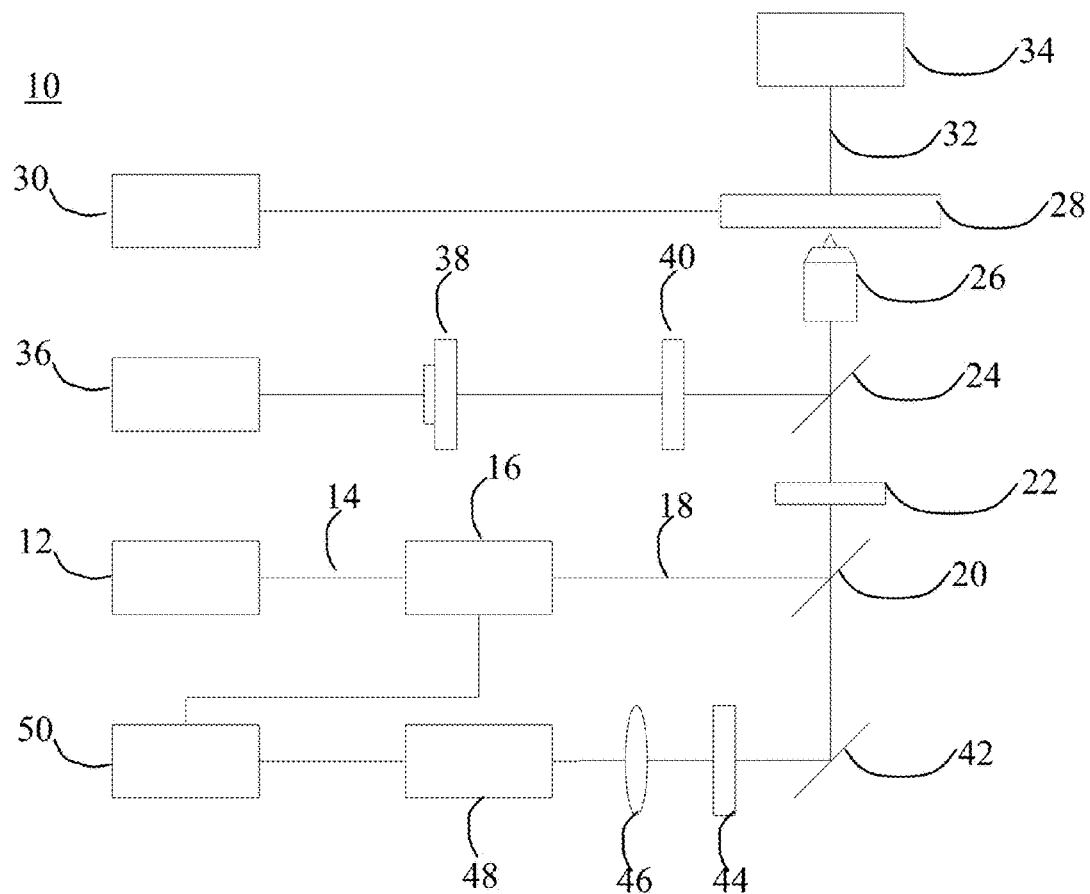
FIG. 1 is a schematic diagram illustrating an embodiment of a system for sorting and manipulation of cells in accordance with the present invention, the system comprising the use of combined holographic optical tweezers and microfluidic chip.

FIG. 1 illustrates the schematic of an embodiment of a cell sorting and manipulation system 10. The system comprises holographic optical tweezers and microfluidic chip device. Light source of the holographic optical tweezers is provided by a continuous-wave laser source 12. In this particular embodiment, the laser source can generate laser with a wavelength of about 1064 nm. The use of this wavelength is to avoid inflicting photo-damage to biological cells. The laser source 12 can provide a laser beam 14 which is sculpted by diffractive optical elements 16 for splitting and steering a single light of beam into multiple beams. In the holographic optical tweezer system, the use of a spatial light modulator (SLM) is preferred. Sculpted laser beams 18 from the optical elements 16 are reflected by a first dichroic mirror 20, and then transmitted through an emission filter 22 and a second dichroic mirror 24 to an inverted microscope objective 26. The inverted microscope objective 26 is not only for use in focusing an optical trap but also capturing an image of a sample. In order to ensure that a stable optical trap is sufficiently stable, an objective lens with high numerical aperture is needed. A microfluidic chip 28 with variable fluidic channel structures is positioned on a sample holder arranged above the microscope objective 26. Particles to be sorted can then be driven into the microfluidic chip by external pumps and valves 30.

The cell sorting and manipulation system 10 also includes an optical imaging system. For bright-field imaging, light 32 from an illuminator 34 provides optical radiation on the microfluidic chip 28 from the above. For fluorescence imaging, an excitation laser source 36 passes through a collimating adapter 38, through the excitation filter 40, reflected by a second dichroic mirror 24, and then focused on the microfluidic chip 28 by the microscope objective 26. The excited fluorescence from the microscope objective 26 passes through the second dichroic mirror 24, through the emission filter 22, through first dichroic mirror 20, reflected by an optional mirror 42 to an optional filter 44 through an imaging lens 46 on a detector 48, such as a CCD camera.

A control system 50 can control the diffractive optical elements 16 to generate one or more optical traps at the desired position and to control the movement of these traps. In addition, the detector 48 combined with the developed image processing method can be coupled to the control system 50 as the feedback to guide the manipulation process of the overall system 10.

Figure 2:
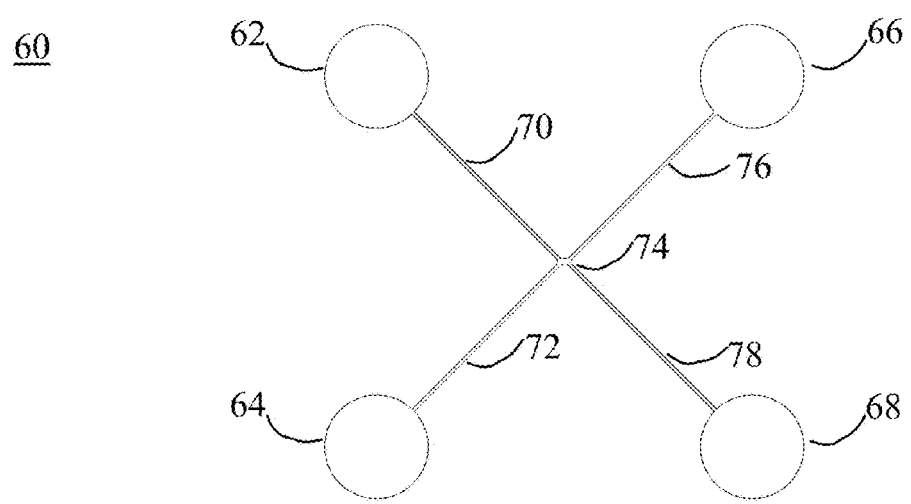
FIG. 2 is a schematic diagram showing a microfluidic channel with a network resembling the English letter "H"

FIG. 2 illustrates a preferred embodiment of a microfluidic channel network 60. The network is generally is considered as a 2×2 fluidic network comprising two inlet reservoirs in that there are provided with a sample reservoir 62 coupled to a sample inlet microfluidic channel 70 and a buffer reservoir 64 coupled to a buffer inlet microfluidic channel 72, and two outlet reservoirs in that there are provided a waste reservoir 66 coupled to a waste outlet microfluidic channel 76 and a the target collection reservoir 68 coupled to a target collection outlet microfluidic channel 78. The inlet channels 70, 72 and the outlet channels 76, 78 are connected together at a cell identification and optical separation branching junction channel 74. In this embodiment, the inlet and outlet microfluidic channels are substantially 30 μm wide and 2000 μm long. The cell identification and optical separation branching junction channel 74 are substantially 60 μm wide and 70 μm long. All the channels are substantially 50 μm deep. The microfluidic chip is designed to provide a substantially 1:1 volumetric pinch ratio by setting the sample inlet flow rate equal to the buffer inlet flow rate. The two-phase laminar flow in the branching junction channel 74 can be established by using two syringe pumps, one connected to the sample inlet reservoir 62 and the other connected to the buffer inlet reservoir 64, with the outlet reservoir 66, 68 at the atmospheric pressure. The syringe pump can be directly connected to the reservoir by tubing for handling both the sample flow and buffer flow.

The microfluidic chip device typically includes a top microfluidic chip layer with micro-channel network and a bottom glass layer. The use of optical tweezers requires that the device be transparent at the wavelength of the laser beam used for cell trapping. In one embodiment, the material used is poly-(di-methyl-siloxine) (PDMS) and the fabrication method is soft lithography technique although other suitable material and fabrication method may be used. The master with microfluidic channel network is created by transferring the shadow ultraviolet (UV)-mask to the spin coated negative photoresist film with certain depth. PDMS mixed 10:1 with the included curing agent is degassed and poured on the master. The optically transparent replica is carried out to obtain the reverse structure of the master after curing. Holes are then punched at the inlet reservoirs and outlet reservoirs using a sharpened syringe needle, and the microfluidic chip is trimmed to the proper size. The bottom glass layer, typically a cover slip, is bonded to the microfluidic chip in the oxygen plasma to form an irreversible seal.

Figure 3:
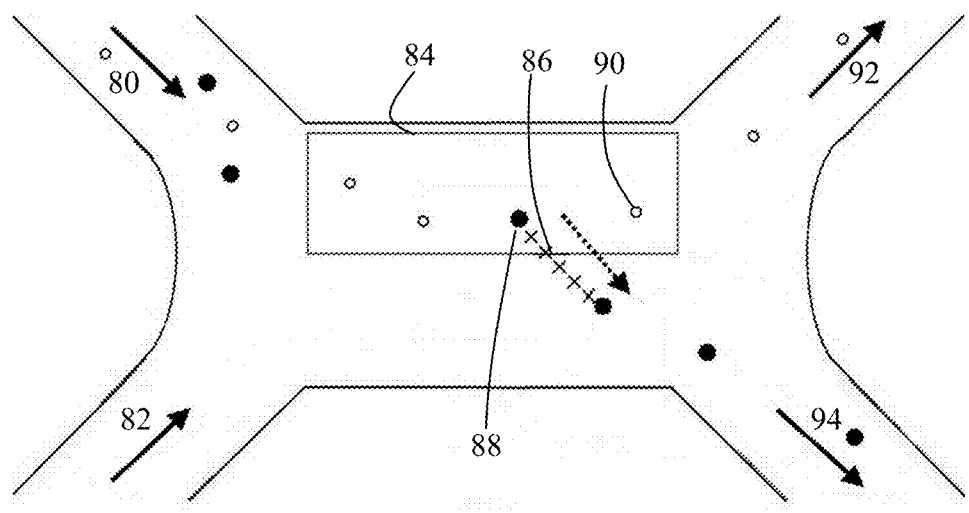
FIG. 3 is an exemplary illustration showing manipulation of a target particle according to an embodiment of methodology of the present invention.

As described above, the microfluidic channel network 60 exhibits a two-phase laminar flow. Optical tweezers are employed to separate the identified target particles away from the sample flow into the collection reservoir with a highly selective manner. A schematic of the operation principle is now described with reference to FIG. 3. The suspended sample flow 80 is one-dimensional focused by a buffer flow 82 to form the two-phase laminar flow in the branching junction channel 74. The particles in the sample flow 80 are then inspected for the presence of desired traits, such as size, morphology, fluorescence or capacitance, by the detector. In one embodiment, the target cells are detected and identified by the CCD camera and image processing techniques. To improve the efficiency of image processing, only a region of interest (ROI) 84 positioned in the sample flow within the branching junction channel 74 is investigated. The optical tweezers are triggered to generate optical traps 86 based on the detection of the target cells 88. The optical traps 86 then move away at any angle relative to the sample flow to translate these target cells 88 into the buffer flow. Finally, the non-target cells 90 flow into the waste reservoir with the sample flow through the waste outlet channel 92, and the target cells 88 flow into the collection reservoir with the buffer flow through the target outlet channel 94.

Two main types of traits may be used to enable efficient triggering of the optical tweezers. One type of trait is based on intrinsic differences, such as cell size, cell shape and cell color, etc. The other type of trait is based on extrinsic differences, such as fluorescence labeling. Charged coupled device (CCD), photomultiplier tube (PMT), and avalanche photodiode (ADP) can be utilized for cell detection and identification. In one embodiment, the CCD combined with image processing technique demonstrates the ability to identify the target cells based on multiple cell features, such as cell size or fluorescence, and also allows the use multi-particle tracking strategy for tracking of multiple particles.

Figure 4:
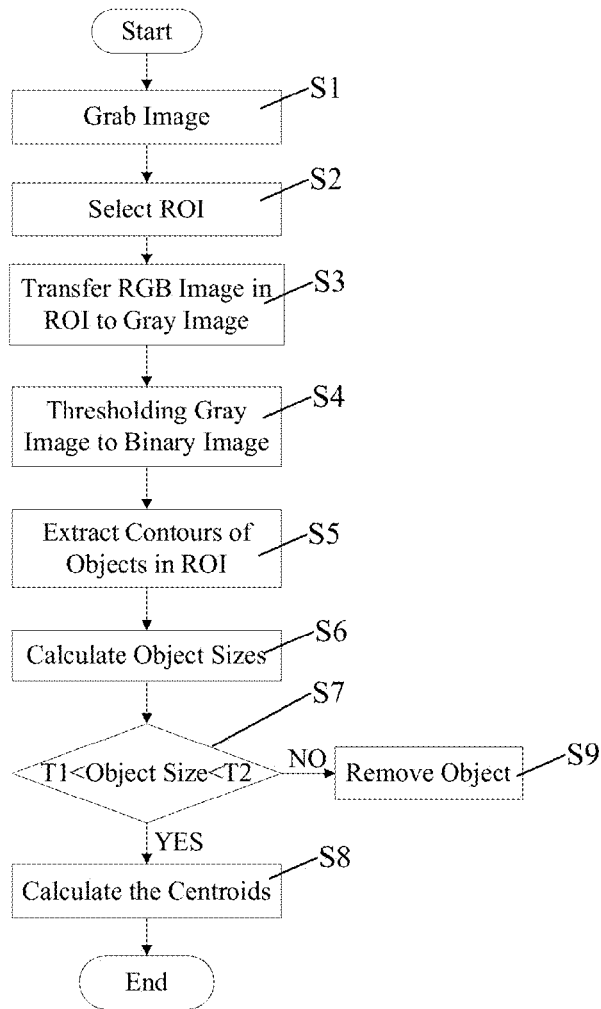
FIG. 4 is a flowchart showing an embodiment of a method of identifying one or more target particles using image processing technique based on the size of the target particles.

FIG. 4 is a flowchart illustrating an embodiment of identification of target particles according to the present invention. Specifically, the embodiment seeks to identify target particles in a particle sample based on different sizes of the particles. FIG. 4 shows a number of processing steps in the identification process. An original color image is captured by a CCD (51), and the ROI is selected to cover the sample flow contained suspended particles with different sizes located in a branching junction channel (S2). In order to improve the efficiency of detection and recognition, only the local color image in ROI is transferred to the gray image (S3). An automatically determined threshold value is applied to realize image binarization and separate the particles from the background (S4). The contours of particles are then extracted from the binary image (S5), and the size of these particles can be calculated from these contours (S6). Determination is then made based on whether a particle being detected is between the minimum size threshold T1 and the maximum size threshold T2 (S7). If the conditions at S7 are met, the centers of the particles can be calculated from the first-order moment of the filled contours (S8). Otherwise, the particles are removed from the image (S9).

Figure 5:
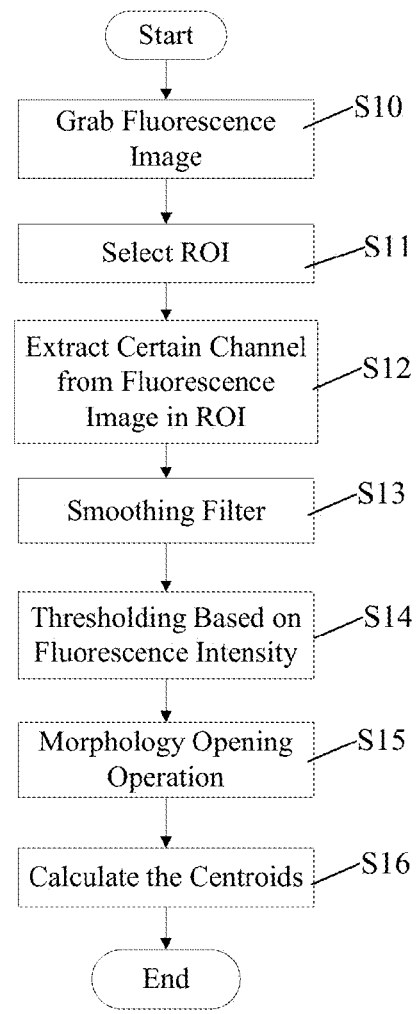
FIG. 5 is a flow chart showing another embodiment of a method of identifying one or more target particles using image processing technique based on fluorescence of the target particles.

FIG. 5 illustrates a similar flowchart of FIG. 4 although the identification of target particles is based on fluorescence labeling. At the beginning of an identification exercise, a fluorescence image is captured by a high-sensitive, low-light fluorescence imaging CCD camera (S10) and the ROI is selected to improve the image processing efficiency (S11). One or more color channels are extracted from the fluorescence image within the ROI based on the fluorescence label on the particles (S12). For example, if green fluorescence proteins (GFP) are labeled on the particles, the green channel of the fluorescence image should be extracted. Smoothing filter is applied on the extracted image to increase the signal-to-noise ratio (S13). According to the intensity of the fluorescence, a suitable threshold is set or predetermined to separate the particles with fluorescence from the low-frequency background (S14). After image binarization, morphology opening operation (erode first and then dilate) is utilized to eliminate the influences of small particles, such as cell fragments or residual stain (S15). Finally, the particles with fluorescence can be detected and located (S16).

To further improve the sorting performance of the present invention in terms of increasing the throughput without the penalty of purity and recovery rate, parallel sorting strategy with multiple independent optical traps is employed. In order to optimize the management of multiple optical traps, it is necessary to distinguish multiple target particles in the ROI by establishing the trajectories of the corresponding particles. Methods for tracking particles in the consecutive frames can be roughly classified into "global pattern" and "local pattern", or "global motion model" and "individual motion model", respectively. The definitions of "global motion model" and "individual motion model" are within the grasp of a skilled person in the art and is addressed in the publication C. J. Veenman, M. J. T. Reinders, and E. Backer, ("Resolving motion correspondence for densely moving points", IEEE Transactions on Pattern Analysis and Machine Intelligence, vol. 23, no. 1, pp. 54-72, January 2001.), content of which is incorporated herein in its entirety.

Studies leading to the present invention indicate that many of the tracking strategies using global motion model pattern perform poorly due to too simplistic assumption of the motion modes of biological particles. In addition, these strategies are too computationally intensive and unsuitable for real-time processing. With the use of individual motion model for particle tracking, more satisfactory results in the low densities and well separated condition. On the other hand, in the context of low density and well separated conditions, using individual motion model for particle tracing can generate more satisfactory results. By "low density", in the context of the aforementioned embodiments the density of the particles is from $10^6$-$10^7$ particles/ml. By well separated, it refers to the condition of the cells not sticking together.

Figure 6:
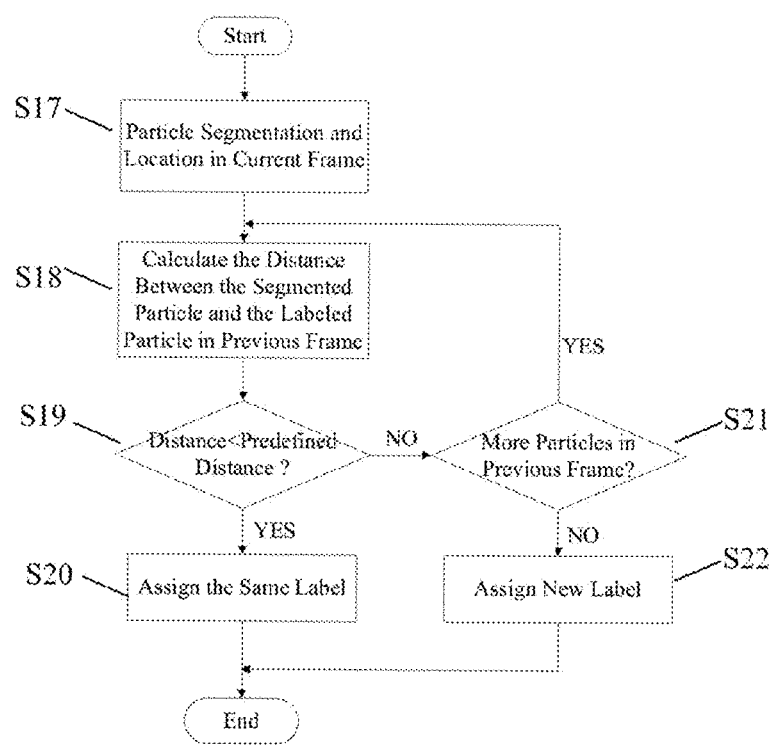
FIG. 6 is a flow chart showing an embodiment of methodology for tracking multiple particles based on model of individual motion tracking.

FIG. 6 is a flowchart showing an embodiment of a multi-particle tracking methodology utilized in the present invention based on individual motion model. With this methodology, once the target particles are detected and recognized, their center positions are recorded based on the index of the current image frame numbers (S17). Then the distance between segmented particle in the current frame and the labeled particles in the previous frame is calculated (S18). Segmented particles refer to individual target particles recognized in the current frame. A determination is made as to whether the calculated distance is less than a predefined distance (S19). If the condition at S19 is satisfied, the target particle in the current frame is assigned the same label as the compared (or referenced) particle in the previous frame (S20). If the target particle does not meet the conditions defined at S19, the method proceeds to S21. At S21, a determination is made as to whether more target particles in previous frame waiting for linking. If the condition is met, the method proceeds to S18 for continued comparison. Otherwise, the target particle in the current frame is assigned a new label (S22).

Once the target particles have been identified and tracked, the optical traps are employed to transport these particles to the destination where they are released. When a target particle is robustly trapped in the flowing fluid, a balance of the force on the vertical plane, including the trapping force of optical trap, buoyant force and gravitational force of the particle is sought. In the horizontal plane, the Langevein force from the Brownian motion of, for example, a target cell particle is very small, and this force can be neglected. Therefore, both the liquid viscous drag force and the optical trapping force in the horizontal plane are imposed on the cell simultaneously during the movement. When the cell moves up to a maximum velocity, its acceleration becomes zero, implying that the fluid drag force and the optical trapping force are equal and opposite. Although in theory the optical traps can move the target particles away from the sample flow at any angle, motion control of the optical traps should be optimized to improve the efficiency of separation.

In a scenario in which a horizontal direction and the flow direction of a target particle are the same, due to the laminar flow within the microfluidic channel the target particle just flows along the branching junction channel in the horizontal direction. When the target particle flows with the fluid, the velocity of the optical trap is designed to match that of the speed of the target particle. Due to the same speed, no trapping force is applied on the particle, which means the energy of the optical trap is not dissipated. The velocity of the target particle can be obtained from calculating the distance d it has moved and the time interval $\Delta t$ between the two consecutive frames. The flow rate of the target particle is then $v=d/\Delta t$.

Figure 7A:
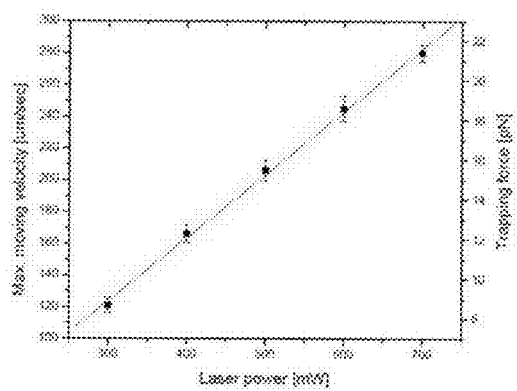
FIGS. 7a-b demonstrate the relationship between maximum moving velocity and trapping force under different laser powers on yeast cells and human embryonic stem cells (hESCs), respectively.
Figure 7B:
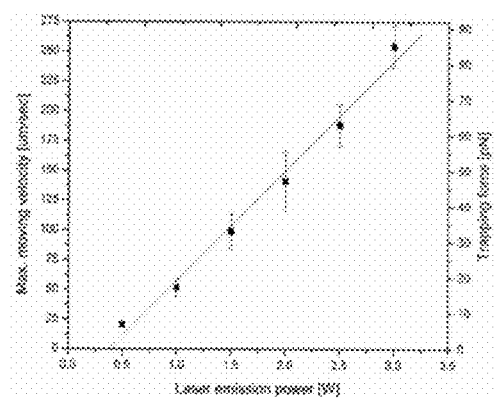

Owing to the laminar nature of microfluidic flow, the fluid velocity perpendicular to the flow direction is zero. In the vertical direction, the optical trap is designed to drive the target particle away from the sample flow as fast as possible without the target particle escaping from the optical trap. The trapping force of the optical trap is approximately proportional to the laser power. However, studies have shown that the temperature increases by about 1-2° C. when using 100 mW optical trap with the wavelength of 1064 nm. To avoid thermal damage to a target particle caused by the optical trap, especially when the particle is a biological cell, a laser power that is as low as possible should be adopted. In order to be able to trap the particle effectively with a low laser power, the relationship between the particle maximum moving velocity and the laser power is calibrated. The maximum moving velocity of a target particle is defined as the velocity at which the particle fails to be trapped, and that velocity can be determined using the viscous-drag-force method by gradually increasing the moving velocity of the motorized stage until the particle escapes from the fixed optical trap. FIGS. 7a-b show the maximum moving velocities and the trapping forces under different laser powers obtained from the tests on yeast cells and human embryonic stem cells (hESCs), respectively. It is to be noted that the laser powers referred to powers output by the laser source, and the actual power at the focus of an optical trap has lost a large fraction of the power during transmission in the process. In applications, moving the optical trap in steps with the distance of each step being the particle radius can result in a quick movement of a trapped target particle.

Figure 8:
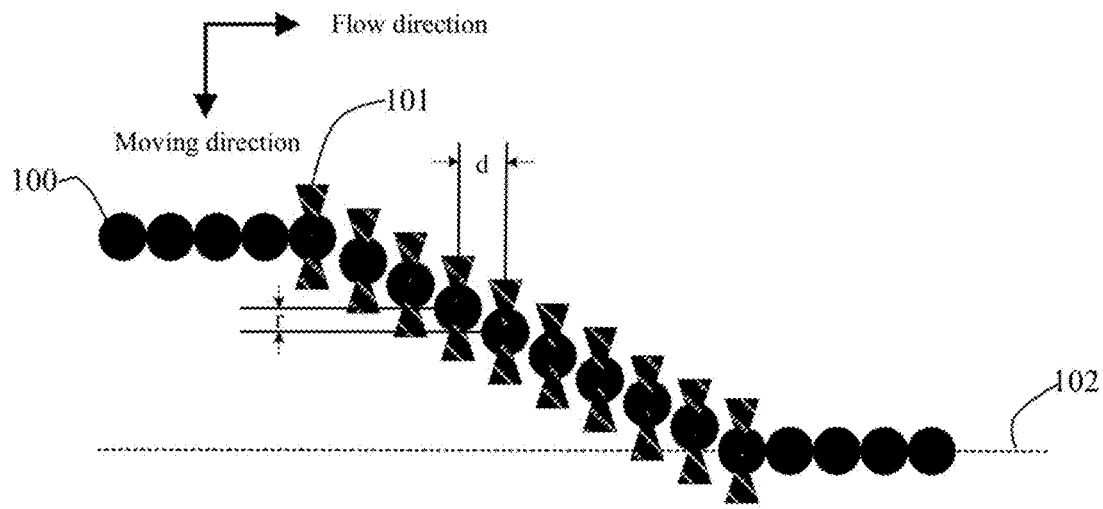
FIG. 8 illustrates, exemplarily, the motion of trajectory of a particle in a flowing fluid and an optically trapped particle according to the present invention.

FIG. 8 shows the motion trajectory of an optically trapped particle in a flowing sample fluid based on the designed motion control of an optical trap. Before the optical trapping, the target particle 100 is transported by the fluid flow horizontally along the branching junction channel. An optical trap 101 is then generated on the target particle 100 to initiate isolation, and then moves the target particle from the sample flow with the moving distance d between the two consecutive frames along the fluid flow in the horizontal direction and the distance of the particle radius r in the vertical direction. The resultant velocity of the target particle combines the dragging velocity of the fluid and the trapping velocity of the optical trap 101, and the target particle 100 can be moved towards destination 102 quickly. After reaching the destination, the optical trap 101 is released from the target particle 100 which finally moves with the buffer flow to a collection reservoir.

Figure 9:
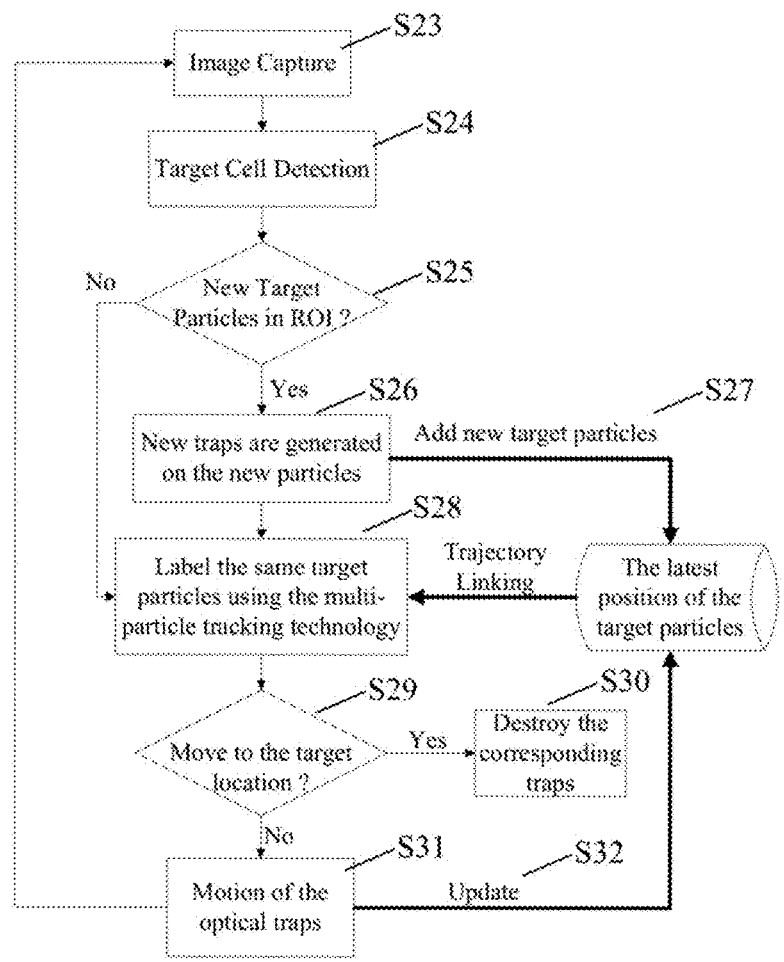
FIG. 9 is a flow chart illustrating an overall process for manipulating flowing of particles according to an embodiment of the present invention.

The above described embodiments allow multi-particle tracking and motion control of optical trap in the fluid flow. FIG. 9 is a flowchart illustrating an overall methodology of whole cell sorting and manipulation. The procedure begins with capturing bright-field or fluorescence image by CCD camera (S23). Corresponding image processing technique as explained above is then utilized to detect and identify a target particle based on predefined intrinsic or extrinsic traits (S24). Determination is made as to whether a new target particle is existed in the ROI (S25). If the condition at S25 is satisfied, a new optical trap is generated on the new target particle (S26). Accordingly, a new label is assigned to the new target particle and stored in the database with its current position (S27). If however the condition at S25 is not satisfied, this result will be compared with the multi-particle tracking result in the previous frame stored in the database (S28) and then a respective or corresponding label will be assigned to the detected target particle in the current frame.

Before moving the optical trap or moving the optical trap further, another determination is made as to whether the trapped target particle has moved to the destination (S29). If the condition at S29 is satisfied, i.e. the target particle has been moved to the destination, the optical trap is released from the target particle, and the label that was used for the target particle is redefined as an unused condition (S30). If the condition at S29 is not satisfied, the trapped target particle is then moved to its new position coordinately by updating the position of the optical trap (S31). It is to be noted that multiple target particles are tracked and moved simultaneously. The new positions of the corresponding labeled target particles are updated (S32) in the database.

EXAMPLES

Experiments were conducted to demonstrate the effectiveness of the aforementioned methodology and are described and discussed as follows.

FIG. 10 shows a series of photographs of isolation of yeast cells (with a diameter of 5-8 μm) from a sample containing and mixed with micro-beads (with a diameter of 2 μm). The yeast cells were completely mixed with the micro-beads at a ratio of 1:1, and then diluted to an acceptable concentration. In this experiment, the yeast cells were defined as the target particles and were to be sorted and collected in the collection reservoir. When the micro-bead moved with the flow of the sample and passed through the ROI, they were identified as the non-targeted particles, and they flowed into the waste channel with the sample flow, as shown in FIGS. 10a-b or more specifically the arrow in FIG. 10b. When the yeast cell passed through the ROI, it was recognized by the system as the target particle and accordingly was trapped, dragged and departed from the sample flow through the optical trap (see for example FIGS. 10c-e) until the yeast cell had reached the destination. Finally, the yeast cell flowed into the collection channel under the driving force of the buffer flow, as shown in FIGS. 10c-f and especially FIG. 10f.

In this experiment, the output laser power was set to substantially 350 mW, and the yeast cell was moved by the optical trap at a velocity of 120 μm/s in the direction perpendicular to the flow. Considering the fluid flow (67 μm/s), the yeast cell was moved to the collection channel at a speed of 137 μm/s.

FIG. 11 shows a series of two successive photographs of sorting multiple yeast cells with multiple independent optical traps in parallel. Specifically, three optical traps were generated at the same time to simultaneously drive three yeast cells identified as target particles in the ROI away from the sample flow. After the yeast cells had arrived at the desired destination, their corresponding or respective optical traps were released from these cells which flowed along with the buffer flow into the collection channel. The maximum number of optical traps available for use simultaneously is determined based on the type of particles or sorted cells to be sorted, the concentration or the particles or cells, and the capacity or limitation of the laser power. The actual number of optical traps employed in a given moment would depend on the number of target particles appeared in the ROI.

FIG. 12 shows a series of two successive photographs of sorting hESCs with GFP (circled cell in figure) from the other cells without fluorescence labels. The size of hESC with GFP is quite similar to that of other non-target particles, such as the differentiated cells, in the mixture. Therefore, if the image processing technique employed in this scenario was based on size difference then this would be unable to distinguish them from the non-target particles. However, the use of fluorescence-based image processing technique can distinguish them. As hESC has a much larger size (i.e., 10-15 μm) than that of yeast cell, higher laser power (1.5 W) can be utilized to supply sufficient trapping force to move hESC particles. The manipulation process is otherwise similar that in the isolation of yeast cells. The hESC with GFP was driven to the collection channel by the optical trap and then flowed into the collection reservoir with the medium flow. The other cells without GFP flow into the waste channel with the sample flow.

The above described experiments and methodology should be understood with reference to conventional cell sorting methods, such as gradient centrifugation, magnetic activated cell sorting (MACS), and fluorescence activated cell sorting (FACS). While these different conventional methods have been widely used and they are effective to the extent that they may be able to generate a relatively high throughput, they require relatively large sample volumes. By a relatively large sample volume, it means the sample having cells (particles) of >100,000 to be separated. On the other hand, by a relatively low sample volume, it means the sample having cells (particles) substantially in the range of 100-100,000 to be separated. To the contrary, methodologies in accordance with the present invention require can still work at least satisfactorily when sorting particles in a small sample population setting. As such, the present invention is particularly advantageous for use in isolating rare cells, such as stem cells or primary cells.

It is to be appreciated that unlike conventional microfluidic optical sorting methods in which the laser or optical trap is generated at a fixed position, embodiments of the present invention do not have this restriction. In other words, the optical trap of the present invention can be generated on the target particle at any position within the region of interest (ROI). Without this restriction, the capability of particle sorting is much enhanced while at the same time the purity of the sorted particles and recovery rate are improved. With the used of moving or movable optical trap, there would be no need for hydro-dynamically focusing the sample flow into a single cell flow for cell separation. Accordingly, complexity or unpredictability arising from fluid control of the sample flow is not necessary. In addition, based on result from detection of target particles, multiple optical traps can be generated simultaneously to achieve multi-cell parallel sorting. Through multi-cell parallel sorting, the throughput of sorting can be increased without the penalty of purity and recovery rate. Further, the present invention allows multi-particle tracking simultaneously over a wide field of view by image processing technique other than the quadrant photo-detector (QPD), and real-time feedback of optical trap control based on individual motion model and not global motion model.

It is also to be noted that the present invention exhibits a recognition capability of multiple features on the target particles with image processing technique. This is to be contrasted with many conventional methods in which recognition of only one specific feature for recognition (e.g., fluorescence) is capable. With such conventional methods, sorting particles with different features would not be possible and accordingly the range of applications would be limited. Since optimization of control of multiple optical traps may be employed in the present invention, multi-particle tracking strategy can be utilized.

Although the present invention as described above is with reference to the specific embodiments, the invention is not intended to be limited to the details described above. Various modifications and improvements can be made according to the certain applications without departing from the invention. It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. Also, a skilled person in the art will be aware of the prior art which is not explained in the above for brevity purpose.

The invention claimed is:

1. A method of manipulating flowing particles, comprising steps of:
   a) providing fluid channels in which a laminar flow of suspended particles moving at constant speed is to be sorted;
   b) providing region of interest in the fluid channels via which the flow of particles pass;
   c) based on methodology of capturing image of the flow of particles, detecting individual first order motions of flowing particles and tracking movement of multiple particles of the flowing particles only in the region of interest by using imaging processing technique suiting capacity of optical trapping means;
   d) based on results from image processing in the step c), determining the presence of at least one target particle from the flow of particles;
   e) based on results from image processing in the step d), labeling center position of the at least one target particle with an index, the index configured for use in tracking movement of multiple particles of flowing particles in comparison with previous frame; and
   f) triggering the generation of an optical trapping means and changing the course of the at least one target particle transversely from a first flow stream to a second flow stream by the optical trapping means;
   wherein the method further comprises steps of:
   i) recording center position of the at least one target particle as current image frame by way of the index; and
   ii) step f), changing the course of the at least one target particle by a series of successive steps, and in each of the successive steps the optical trapping means is adapted to move the at least one target particle by a distance equal to the radius of the target particle and perpendicular to the laminar flow;
   wherein the velocity of the optical trap and the velocity of the laminar flow in the direction of the laminar flow along branching junction of the fluid channels are substantially the same; and
   wherein the optical trapping means includes at least one optical trap, and the number of optical traps employed corresponds to the number of detected target particles in the region of interest and the capacity of the optical trapping means.

2. A method as claimed in claim 1, comprising moving the at least one target particle to a target location by the optical trap.

3. A method as claimed in claim 2, comprising determining whether the at least one target particle has been moved to the target location, and if the at least one target particle has been moved to the target location the optical trapping means is released from the target particle, and if the at least one target particle has not been moved to the target location data associated with current position of the target particle(s) is updated within a database.

4. A method as claimed in claim 1, wherein, in step (e), comprising steps of:
   (i) calculating the distance between the at least one target particle in current image frame and a respective labeled particle in previous image frame;
   (ii) ascertaining whether the distance in step (i)) is less than a predefined distance; and
   (iii) assigning same label of the respective labeled particle for the at least one target particle in current frame if the distance in step (ii) is less than the predefined distance; or assigning new label for the at least one target particle in current frame if the distance in step (ii) is equal or greater than the predefined distance.

5. A method as claimed in claim 1, wherein, in step c), the image processing technique is adapted to identify particles based on intrinsic features such as morphology and sizes of the particles.

6. A method as claimed in claim 1, wherein, in step c), the image processing technique is adapted to identify particles based on extrinsic features such as fluorescence labeling and tagging on the particles.

7. A method as claimed in claim 1, comprising a step of measuring the velocity of the at least one target particle in the laminar flow.

8. A method as claimed in claim 1, comprising a step of providing a branching junction in the fluid channels, wherein the at least one optical trap is movable or moves diagonally along the branching junction for translating the at least one target cell into a target channel of the fluid channels.

9. A system for sorting target particles from a flow of particles, comprising:
   a) a microscope;
   b) a light source;
   c) a CCD camera;
   d) microfluidic chip device with microfluidic channels;
   e) a detection apparatus for detecting the target particles with predefined specific features;
   f) a response generating apparatus adapted to generate a signal in response to the detection of the target particles only in a region of interest; and
   g) an optical tweezing system for controlling movement of optical traps, said optical tweezing system is operably linked to the response signal;
   wherein the detection apparatus includes means for labelling the target particles with a reference index for comparison; and
   wherein the optical tweezing system includes at least one optical trap, and the number of optical traps employed corresponds to the number of detected target particles in the region of interest and the capacity of the optical trapping means.

10. An apparatus as claimed in claim 9, wherein the microfluidic chip device includes a cover glass layer, a PDMS microfluidic chip layer and a fluid flow controller.

11. An apparatus as claimed in claim 10, wherein the PDMS microfluidic chip layer is provided with a plurality of reservoirs and a plurality of the microfluidic channels.

12. The apparatus as defined in claim 10, wherein said optical tweezing system includes holographic optical tweezers.

13. A method of manipulating flowing particles, comprising steps of:
   a) providing fluid channels in which a laminar flow of suspended particles moving at constant speed is to be sorted;
   b) providing region of interest in the fluid channels via which the flow of particles pass;
   c) based on methodology of capturing image of the flow of particles, detecting individual first order motions of flowing particles and tracking movement of multiple particles of the flowing particles only in the region of interest by using imaging processing technique for suiting capacity of optical trapping means;
   d) based on results from image processing in the step c), determining the presence of at least one target particle from the flow of particles;
   e) based on results from image processing in the step d), labelling center position of the at least one target particle with a index, the index configured for tracking movement of multiple particles of the flowing particles in comparison of previous frame; and f) triggering the generation of the optical trapping means and changing the course of the at least one target particle transversely from a first flow stream to a second flow stream by the optical trapping means;

wherein the optical trapping means includes at least one optical trap, and the number of optical traps employed corresponds to the number of detected target particles in the region of interest and the capacity of the optical trapping means.

\* \* \* \* \*